(12) United States Patent
Jaekel et al.

(10) Patent No.: US 10,975,334 B2
(45) Date of Patent: Apr. 13, 2021

(54) PROCESS FOR MANUFACTURING GRANULES

(71) Applicant: BASF SE, Ludwigshafen am Rhein (DE)

(72) Inventors: Frank Jaekel, Mannheim (DE); Michael Klemens Mueller, Hassloch (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/060,148

(22) PCT Filed: Dec. 1, 2016

(86) PCT No.: PCT/EP2016/079360
§ 371 (c)(1),
(2) Date: Jun. 7, 2018

(87) PCT Pub. No.: WO2017/097657
PCT Pub. Date: Jun. 15, 2017

(65) Prior Publication Data
US 2018/0355285 A1 Dec. 13, 2018

(30) Foreign Application Priority Data

Dec. 11, 2015 (EP) ..................... 15199496

(51) Int. Cl.
| | | |
|---|---|---|
| *C11D 3/33* | (2006.01) | |
| *C11D 11/00* | (2006.01) | |
| *C11D 11/02* | (2006.01) | |
| *C11D 7/32* | (2006.01) | |
| *C11D 3/20* | (2006.01) | |
| *C11D 3/04* | (2006.01) | |
| *C07C 227/40* | (2006.01) | |

(52) U.S. Cl.
CPC ............. *C11D 3/33* (2013.01); *C07C 227/40* (2013.01); *C11D 3/046* (2013.01); *C11D 3/2075* (2013.01); *C11D 7/3245* (2013.01); *C11D 11/0082* (2013.01); *C11D 11/02* (2013.01)

(58) Field of Classification Search
None
See application file for complete search history.

(56) References Cited

U.S. PATENT DOCUMENTS

| | | | | |
|---|---|---|---|---|
| 5,519,948 A | * | 5/1996 | Raehse | ............... B01D 1/18 34/347 |
| 6,845,571 B1 | * | 1/2005 | Schwarz | ............... B01J 2/04 34/372 |
| 2011/0054215 A1 | | 3/2011 | Euser et al. | |
| 2012/0046491 A1 | | 2/2012 | Mrzena et al. | |
| 2012/0149936 A1 | | 6/2012 | Baranyai | |
| 2012/0202731 A1 | * | 8/2012 | Mrzena | ............... C11D 11/0088 510/224 |
| 2014/0073554 A1 | | 3/2014 | Van Der Eerden et al. | |
| 2016/0221930 A1 | | 8/2016 | Baranyai | |
| 2016/0376529 A1 | | 12/2016 | Van Der Eerden et al. | |

FOREIGN PATENT DOCUMENTS

| | | |
|---|---|---|
| DE | 102009038951 A1 | 3/2011 |
| GB | 2491619 A | 12/2012 |
| WO | WO 2009/103822 A1 | 8/2009 |
| WO | WO 2012/041741 A1 | 4/2012 |
| WO | WO 2012/168739 A1 | 12/2012 |
| WO | WO 2015/121170 A1 | 8/2015 |

OTHER PUBLICATIONS

International Preliminary Report on Patentability dated Oct. 20, 2017 in PCT/EP2016/079360, filed on Dec. 1, 2016.
International Search Report dated Feb. 22, 2017 in PCT/EP2016/079360, filed on Dec. 1, 2016.
Extended European Search Report dated Jun. 10, 2016 in Patent Application No. 15199496.9.

* cited by examiner

*Primary Examiner* — Katie L. Hammer
(74) *Attorney, Agent, or Firm* — Arent Fox LLP

(57) ABSTRACT

Process for manufacturing granules of at least one alkali metal salt of aminopolycarboxylic acid (A), comprising the steps of (a) providing an aqueous slurry of alkali metal salt of aminopolycarboxylic acid (A), (b) maintaining said aqueous slurry at a temperature in the range of from 50 to 90° C. over a period of time in the range of from 2 to 180 hours, (c) spray granulating said slurry with a gas inlet temperature of at least 150° C.

12 Claims, No Drawings

PROCESS FOR MANUFACTURING GRANULES

The present invention is directed towards a process for manufacturing granules of at least one alkali metal salt of aminopolycarboxylic acid (A), comprising the steps of
(a) providing an aqueous slurry of alkali metal salt of aminopolycarboxylic acid (A),
(b) maintaining said aqueous slurry at a temperature in the range of from 50 to 90° C. over a period of time in the range of from 2 to 180 hours,
(c) spray granulating said slurry with a gas inlet temperature of at least 150° C.

Chelating agents of the aminopolycarboxylate type such as methyl glycine diacetic acid (MGDA) and glutamic acid diacetic acid (GLDA) and their respective alkali metal salts are useful sequestrants for alkaline earth metal ions such as $Ca^{2+}$ and $Mg^{2+}$. A lot of aminopolycarboxylates show good biodegradability and are thus environmentally friendly. For that reason, they are recommended and used for various purposes such as laundry detergents and for automatic dishwashing (ADW) formulations, in particular for so-called phosphate-free laundry detergents and phosphate-free ADW formulations.

Depending on the type of product—liquid home care and fabric care products versus solid home care and fabric care products—and the manufacturing process of solid home care and fabric care products care product manufacturers may either prefer to handle solutions of aminopolycarboxylates or solid aminopolycarboxylates, for example joint spray drying or solid mixing. Powders and granules of aminopolycarboxylates may be shipped economically due to their high active ingredient content that goes along with low water content. Therefore, convenient processes for providing granules are still of great commercial interest.

In WO 2009/103822, a process is disclosed in which slurries are granulated that have a certain solids content, with a gas inlet temperature of 120° C. or less.

In WO 2012/168739, a process is disclosed wherein slurries of complexing agents are spray-dried under non-agglomerating conditions.

Both processes have their shortcomings. A low gas inlet temperature requires highly concentrated slurries or a huge amount of gas per unit of granule. A process using non-agglomerating conditions only provides for powders.

It was therefore the objective of the present invention to provide a process for manufacturing granules of alkali metal salts of aminopolycarboxylic acids that is economically advantageous, said granule having excellent properties.

Accordingly, the process defined at the outset has been found, said process hereinafter also being referred to as process according to the invention or—briefly—as inventive process.

The inventive process concerns manufacturing granules of at least one alkali metal salt of aminopolycarboxylic acid (A).

The term "granule" in the context of the present invention refers to particulate materials that are solids at ambient temperature and that preferably have an average particle diameter (D50) in the range of from 0.1 mm to 2 mm, preferably 0.4 mm to 1.25 mm. The average particle diameter of inventive granules can be determined, e.g., by optical or preferably by sieving methods. Sieves employed may have a mesh in the range of from 60 to 3,000 µm.

In one embodiment of the present invention, granules have a broad particle diameter distribution. In another embodiment of the present invention, granules may have a narrow particle diameter distribution. The particle diameter distribution may be adjusted, if desired, by multiple sieving steps.

Granules may contain residual moisture, moisture referring to water including water of crystallization and adsorbed water. The amount of water may be in the range of from 0.1 to 20% by weight, preferably 1 to 15% by weight, referring to the total solids content of the respective powder or granule, and may be determined by Karl-Fischer-titration or by drying at 160° C. to constant weight with infrared light.

Particles of granules may have regular or irregular shapes. Preferred shapes of particles of granules are spheroidal shapes.

The inventive process comprises three steps, hereinafter in brief also referred to as step (a), step (b) and step (c).

Step (a) refers to providing an aqueous slurry of alkali metal salt of aminopolycarboxylic acid (A). Said slurry comprises a continuous phase and solids slurried in said continuous phase. The continuous phase of the slurry provided in step (a) comprises water and aminopolycarboxylic acid (A), and it is a saturated solution of aminopolycarboxylic acid.

The concentration of alkali metal salt of aminopolycarboxylic acid (A) in the continuous phase depends on the temperature of the slurry, on the nature of alkali metal salt of aminopolycarboxylic acid (A), and on additives that may be present in the slurry provided in step (a).

Solids in the slurry are mainly particles of alkali metal salt of aminopolycarboxylic acid (A). In one embodiment of the present invention, solids in the slurry provided in step (a) are at least 75% by weight aminopolycarboxylic acid (A). In another embodiment of the present invention, solids in the slurry provided in step (a) are composed from aminopolycarboxylic acid (A). In yet another embodiment of the present invention, at least 75% by weight of the solids in the slurry provided in step (a) are aminopolycarboxylic acid (A) and up to 25% by weight are an additive, additives being discussed further down below.

In any way, minor amounts of aminopolycarboxylic acid (A) may bear a cation other than alkali metal. It is thus possible that minor amounts, such as 0.01 to 5 mol-% of total aminopolycarboxylic acid (A) bear alkali earth metal cations such as $Mg^{2+}$ or $Ca^{2+}$, or an $Fe^{2+}$ or $Fe^{3+}$ cation.

In one embodiment of the present invention, alkali metal salt of aminopolycarboxylic acid (A) may contain one or more impurities that may result from the production of the respective chelating agent. In the case of MGDA and its alkali metal salts, such impurities may be selected from propionic acid, lactic acid, alanine, nitrilotriacetic acid (NTA) or the like and their respective alkali metal salts. Such impurities are usually present in minor amounts. "Minor amounts" in this context refer to a total of 0.1 to 5% by weight, referring to alkali metal salt of aminopolycarboxylic acid (A), preferably up to 2.5% by weight. In the context of the present invention, such minor amounts are neglected when determining the composition of granule made according to the inventive process.

Alkali metal salts of aminopolycarboxylic acid (A) may be selected from compounds that bear at least one amino group per molecule and at least two carboxyl groups, partially or fully neutralized with alkali metal cations, same or different, for example cations of lithium, sodium, potassium, rubidium, cesium, and combinations of at least two of the foregoing. Preferred examples of alkali metal cations are sodium and potassium and combinations of sodium and potassium.

Preferred examples of alkali metal salts of aminopolycarboxylic acids (A) are compounds according to general formula (I)

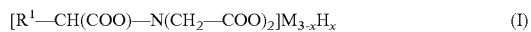

wherein

M is selected from alkali metal cations, same or different, for example cations of lithium, sodium, potassium, rubidium, cesium, and combinations of at least two of the foregoing. Preferred examples of alkali metal cations are sodium and potassium and combinations of sodium and potassium.

x is in the range of from zero to 1.0, preferred are zero to 0.5. In a particularly preferred embodiment, x is zero.

$R^1$ is selected from $C_1$-$C_4$-alkyl, for example methyl, ethyl, iso-propyl, sec.-butyl and iso-butyl, preferably methyl.

In one embodiment of the present invention, aminopolycarboxylic acid (A) is selected from compounds according to general formula (II)

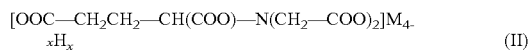

wherein

M is selected from alkali metal cations, same or different, as defined above, x is in the range of from zero to 2.0, preferred are zero to 0.5. In a particularly preferred embodiment, x is zero.

In the context of the present invention, alkali metal salts of methylglycine diacetic acid ("MGDA") are selected from lithium salts, potassium salts and preferably sodium salts of MGDA. MGDA can be partially or preferably fully neutralized with the respective alkali. In a preferred embodiment, an average of from 2.7 to 3 COOH groups of MGDA is neutralized with alkali metal, preferably with sodium. In a particularly preferred embodiment, chelating agent (A) is the trisodium salt of MGDA.

MGDA and its respective alkali metal salts can be selected from the racemic mixtures, the D-isomers and the L-isomers, and from mixtures of the D- and L-isomers other than the racemic mixtures. Preferably, MGDA and its respective alkali metal salts are selected from the racemic mixture and from mixtures containing in the range of from 55 to 85 mole-% of the L-isomer, the balance being D-isomer. Particularly preferred are mixtures containing in the range of from 60 to 80 mole-% of the L-isomer, the balance being D-isomer.

In one embodiment of the present invention alkali metal salts of aminopolycarboxylic acids (A) are selected from alkali metal salts of methylglycine diacetic acid and glutamic acid diacetic acid. In a preferred embodiment of the present invention, alkali metal salts of aminopolycarboxylic acids (A) are selected from sodium and potassium salts of methylglycine diacetic acid and glutamic acid diacetic acid, in each case fully neutralized.

In one embodiment of the present invention, such aqueous slurry provided according to step (a) has a pH value in the range of from 8 to 14, preferably from 9 to 13.5 and even more preferably at least 9.5. The pH value is determined at ambient temperature and refers to the continuous phase.

The aqueous slurry provided in step (a) may have a temperature in the range of from 15 to 85° C., preferably 20 to 80° C.

Providing an aqueous slurry of alkali metal salt of aminopolycarboxylic acid (A) may be achieved in various ways. In a preferred embodiment, solid particulate alkali metal salt of aminopolycarboxylic acid (A) is added to an aqueous solution of alkali metal salt of aminopolycarboxylic acid (A) in amount that the maximum solubility of alkali metal salt of aminopolycarboxylic acid (A) in water is exceeded. Said solid particulate alkali metal salt of aminopolycarboxylic acid (A) may be amorphous or at least partially crystalline, see, e.g., US 2012/0046491.

In one embodiment of the present invention, step (a) is performed by providing an aqueous solution of alkali metal salt of aminopolycarboxylic acid (A) and removing some of the water so that a slurry forms, for example by evaporation or distilling off some of the water.

In a preferred embodiment of the present invention, solid particulate alkali metal salt of aminopolycarboxylic acid (A) is selected from the fines usually created in the course of a spray-granulating process and from ground lump particles created in the course of a spray-granulating process each of alkali metal salt of aminopolycarboxylic acid (A). For that reason, solid particulate alkali metal salt of aminopolycarboxylic acid (A) in aqueous slurry provided in step (a) preferably has a bimodal particle diameter distribution. The average particle diameter (D50) of such solid particulate alkali metal salt of aminopolycarboxylic acid (A) may is preferably 200 μm or less, even more preferably in the range of from 15 to 150 μm.

Grinding of lumps of alkali metal salt of aminopolycarboxylic acid (A) may be performed in any type of mills. Examples of particularly useful mills are jet mills and bolting machines (German: Stiftmühle).

In step (b), the aqueous slurry provided in accordance with step (a) is maintained at a temperature in the range of from 50 to 90° C. over a period of time in the range of from 2 to 180 hours.

In a preferred embodiment of step (b), the aqueous slurry provided in accordance with step (a) is maintained at a temperature in the range of from 50 to 90° C. over a period of time of at least three hours up to 10 hours.

In a preferred embodiment of step (b), the aqueous slurry provided in accordance with step (a) is maintained at a temperature in the range of from 75 to 90° C. over a period of time in the range of from 2 to 180 hours, preferably 3 to 10 hours. Even more preferably, the aqueous slurry provided in accordance with step (a) is maintained at a temperature in the range of from 60 to 85° C. over a period of time in the range of from 2 to 180 hours, preferably 3 to 10 hours.

Step (b) may be performed with or without agitation. Preferably, step (b) is performed with agitation. Agitation may be accomplished, for example, by mechanical stirring, for example with a stirrer. The effect of stirring may be supported by baffles.

In a special embodiment of step (b) water is added. However, water is only added to an extent that no clear solution is formed.

In the context of the present invention, step (b) may also be referred to as aging step, and the aqueous slurry obtained after step (b) may also be referred to as aged aqueous slurry.

Step (c) of the inventive process refers to spray granulating said slurry with a gas inlet temperature of at least 150° C. The gas inlet temperature refers to the so-called "hot gas": The hot gas may be nitrogen, a rare gas or preferably air. In the course of step (c), most of the water of the aged aqueous slurry will be removed, for example at least 55%, preferably at least 65% of the water. In one embodiment of the present invention, 99% of the water at most will be removed. Spray granulating is a method of removing water under agglomerating conditions.

Said spray granulation will be described in more detail below.

In one embodiment of the present invention, a drying vessel, for example a spray chamber or a spray tower, is being used in which step (c) is being performed by using a fluidized bed. Such a drying vessel is charged with a fluidized bed of alkali metal salt of aminopolycarboxylic acid (A), obtained by any drying method such as spray drying or evaporation crystallization or spray granulation, and a slurry of alkali metal salt of aminopolycarboxylic acid (A) is sprayed onto or into such fluidized bed together with a hot gas stream. The hot gas inlet stream may have a temperature in the range of from at least 150° C., preferably 150 to 350° C., even more preferably 160 to 220° C.

In one embodiment of the present invention, the fluidized bed may have a temperature in the range of from 80 to 150° C., preferably 85 to 110° C.

Spraying is being performed through one or more nozzles per drying vessel. Suitable nozzles are, for example, high-pressure rotary drum atomizers, rotary atomizers, single-fluid nozzles and two-fluid nozzles, two-fluid nozzles and rotary atomizers being preferred. The first fluid is the aged aqueous slurry, the second fluid is compressed hot gas, for example with a pressure of 1.1 to 7 bar.

In one embodiment of the present invention, the droplets formed during the spray-granulating have an average diameter in the range of from 10 to 500 µm, preferably from 20 to 180 µm, even more preferably from 30 to 100 µm.

In one embodiment of the present invention, the off-gas departing the drying vessel may have a temperature in the range of from 40 to 140° C., preferably 80 to 110° C. but in any way colder than the hot gas stream. Preferably, the temperature of the off-gas departing the drying vessel and the temperature of the solid product present in the drying vessel are identical.

In another embodiment of the present invention, spray-granulation is being performed by performing two or more consecutive spray-drying processes, for example in a cascade of at least two spray dryers, for example in a cascade of at least two consecutive spray towers or a combination of a spray tower and a spray chamber, said spray chamber containing a fluidized bed. In the first dryer, a spray-drying process is being performed in the way as follows.

Spray-drying may be preferred in a spray dryer, for example a spray chamber or a spray tower. An aged aqueous slurry with a temperature preferably higher than ambient temperature, for example in the range of from 50 to 95° C., is introduced into the spray dryer through one or more spray nozzles into a hot gas inlet stream, for example nitrogen or air, the solution or slurry being converted into droplets and the water being vaporized. The hot gas inlet stream may have a temperature in the range of from 125 to 350° C.

The second spray dryer is charged with a fluidized bed with solid from the first spray dryer and solution or slurry obtained according to the above step is sprayed onto or into the fluidized bed, together with a hot gas inlet stream. The hot gas inlet stream may have a temperature in the range of from 125 to 350° C., preferably 160 to 220° C.

In one embodiment of the present invention, especially in a process for making an inventive granule, the average residence time of alkali metal salt of aminopolycarboxylic acid (A) in step (c) is in the range of from 2 minutes to 4 hours, preferably from 30 minutes to 2 hours.

In one embodiment of the present invention, the pressure in the drying vessel in step (c) is normal pressure ±100 mbar, preferably normal pressure ±20 mbar, for example one mbar less than normal pressure.

In one embodiment of the present invention, the aqueous slurry subjected to spray-granulation in step (c) further contains at least one additive selected from silica, silicates, inorganic salts, complexing agents other than aminopolycarboxylic acid (A) and organic (co)polymers. Such additive (s) may also be referred to as additive(s) (B). This may be accomplished by adding one or more additives (B) to the aqueous slurry at any stage before step (c). Examples of useful additives (B) are, for example, titanium dioxide, sodium carbonate, potassium carbonate, sugar, silica gel, sodium silicate, potassium silicate, and (co)polymers such as, but not limited to polyacrylates, polyalkylenimines such as polyethylenimines, alkoxylated polyethylenimines, carboxymethylated polyethylenimines, and polyvinyl alcohol. Polyvinyl alcohol in the context of the present invention refers to completely or partially hydrolyzed polyvinyl acetate. In partially hydrolyzed polyvinyl acetate, at least 95 mol-%, preferably at least 96 mol-% of the acetate groups have been hydrolyzed. Examples of complexing agents other than aminopolycarboxylic acid (A) are alkali metal citrates. Another possible class of additives is phosphonates, for example the alkali metal salts of 1-hydroxyethane 1,1-diphosphonic acid, "HEDP".

In one embodiment of the present invention polyvinyl alcohol has an average molecular weight $M_w$ in the range of from 22,500 to 115,000 g/mol, for example up to 40,000 g/mol.

In one embodiment of the present invention polyvinyl alcohol has an average molecular weight $M_n$ in the range of from 2,000 to 40,000 g/mol.

In one embodiment of the present invention, the aqueous slurry subjected to spray-granulation in step (c) contains 0.05 to 30% by weight of additive(s) (B) in total, the percentage referring to the entire aqueous slurry. The amount of polyethylenimines or alkoxylated polyethylenimines is preferably in the range of from 0.05 to 0.5% by weight, the amount of silicate may be up to 30% by weight.

One or more additional steps (d) may be performed at any stage of the inventive proves, preferably after step (c). It is thus possible to perform a sieving step (d) to remove lumps from the powder or granule. Also, a post-drying step (d) is possible. Air classifying may be performed during or after step (c) to remove fines.

Fines, especially those with a diameter of less than 50 µm, may deteriorate the flowing behavior of powders or granules obtained according to the inventive process. However, amorphous or preferably crystalline fines may be returned to the spray vessel(s) as seed for crystallization. Lumps may be removed and either re-dissolved in water or milled and used as seed for crystallization in the spray vessel(s).

The inventive process furnishes granules containing alkali metal salt of aminopolycarboxylic acid (A) and, optionally, one or more additives (B). Such granules exhibit overall advantageous properties including but not limited to an excellent yellowing behavior and excellent percarbonate stability. Such granules may be used for making laundry care formulations and hard surface cleaners including, but not limited to automatic dishwashing detergents.

The current invention is further illustrated by working examples.

Note: Average particle diameters are (D50) values and are determined by sieving methods unless expressly noted otherwise.

EXAMPLE 1

Step (a.1): an aqueous slurry of MGDA-Na$_3$ (65% L-MGDA-Na$_3$, 35% D-MGDA-Na$_3$) was made by charging a vessel with 10.9 kg of a 40% by weight aqueous solution of MGDA-Na$_3$ and heating it to 80° C. An amount of 4.1 kg MGDA-Na$_3$ powder, amorphous, manufactured by non-agglomerative spray-drying, average particle diameter (D50) 15 µm, is added. After 30 minutes, an amount of 1.8 kg of water is added. An aqueous slurry is obtained.

Step (b.1): the aqueous slurry obtained in accordance with step (a.1) is stirred for 3 hours at 80° C. An aged aqueous slurry is obtained.

Step (c.1):

A vessel containing a fluidized bed from 1 kg of solid MGDA-Na$_3$ granule, initial average particle diameter 550 µm, is provided. The fluidization is accomplished by entering a so-called fluidization gas at the bottom of the vessel, said fluidization gas being air with an inlet temperature of 150° C.

As soon as the bed temperature of at least 105° C. is reached, an amount of 2 kg/h of aged aqueous slurry according to step (b.1) is sprayed onto the fluidized bed with the help of a nozzle. The spraying—and thus atomizing—is accomplished with air with a gas inlet temperature of 150° C. Every 30 minutes an aliquot of granule is removed from the vessel, and classified by sieving. The fines—particle diameter of 350 µm or below—may be used as particulate solid for making more aqueous slurry according to step (a.1). The lumps—particle diameter more than 1.5 mm—may be milled and mixed with the fines before using them in step (a.1).

A free-flowing granule of MGDA-Na$_3$ is obtained that has excellent properties such as, but not limited to excellent percarbonate stability and low hygroscopicity. No hot spots are observed during processing. No sticky material is obtained.

EXAMPLE 2

Basically, example 1 is repeated but with step (a.2) instead of step (a.1).

Step (a.2): an aqueous slurry of racemic MGDA-Na$_3$ was made by charging a vessel with 10.9 kg of a 40% by weight aqueous solution of MGDA-Na$_3$ and heating it to 80° C. An amount of 4.1 kg MGDA-Na$_3$ powder, crystalline, modification 1, manufactured by spray-granulation followed by milling, average particle diameter (D50) 65 µm, is added. After 30 minutes, an amount of 1.8 kg of water is added. An aqueous slurry is obtained.

Step (b.2): the aqueous slurry obtained in accordance with step (a.2) is stirred for 3 hours at 80° C. An aged aqueous slurry is obtained.

Step (c.2):

The protocol of step (c.1) is followed but aged aqueous slurry according to step (b.2) is used.

A free-flowing granule of MGDA-Na$_3$ is obtained that has excellent properties such as, but not limited to excellent percarbonate stability and low hygroscopicity. No hot spots are observed during processing. No sticky material is obtained.

EXAMPLE 3

Basically, example 1 is repeated but with step (a.3) instead of step (a.1).

Step (a.3): an aqueous slurry of MGDA-Na$_3$ (60% L-MGDA-Na$_3$, 40% D-MGDA-Na$_3$) was made by charging a vessel with 10.9 kg of a 40% by weight aqueous solution of MGDA-Na$_3$ and heating it to 80° C. An amount of 4.1 kg MGDA-Na$_3$ powder, crystalline, modification 2, manufactured by spray-granulation followed by milling, average particle diameter (D50) 50 µm is added. After 30 minutes, an amount of 1.8 kg of water is added. An aqueous slurry is obtained.

Step (b.3): the aqueous slurry obtained in accordance with step (a.3) is stirred for 3 hours at 80° C. An aged aqueous slurry is obtained.

Step (c.3):

The protocol of step (c.1) is followed but aged aqueous slurry according to step (b.3) is used.

A free-flowing granule of MGDA-Na$_3$ is obtained that has excellent properties such as, but not limited to excellent percarbonate stability and low hygroscopicity. No hot spots are observed during processing. No sticky material is obtained.

The invention claimed is:

1. A process for manufacturing granules from an aqueous slurry of at least one alkali metal salt of aminopolycarboxylic acid (A) under agglomerating conditions, comprising:
    (a) providing an aqueous slurry of alkali metal salt of aminopolycarboxylic acid (A),
    (b) maintaining said aqueous slurry at a temperature in a range of from 50 to 90° C. over a period of time in a range of from 2 to 180 hours, and
    (c) spray granulating said slurry with a gas inlet temperature of at least 150° C. for an average residence time ranging from 2 minutes to 4 hours, to obtain granules of the at least one alkali metal salt of aminopolycarboxylic acid (A) having an average particle diameter (D50) in the range of from 0.4 mm to 2 mm.

2. The process according to claim 1, wherein said aqueous slurry provided in (a) has a concentration of (A) in a range of from 45 to 65% by weight.

3. The process according to claim 1, wherein the alkali metal salts of aminopolycarboxylic acids (A) are selected from alkali metal salts of methylglycine diacetic acid and glutamic acid diacetic acid.

4. The process according to claim 1, wherein the alkali metal salts of aminopolycarboxylic acids (A) are selected from sodium and potassium salts of methylglycine diacetic acid and glutamic acid diacetic acid, in each case fully neutralized.

5. The process according to claim 1, wherein the aqueous slurry in (b) is maintained at the temperature range with or without agitation.

6. The process according to claim 1, wherein the aqueous slurry in (b) is maintained at a temperature in a range of from 60 to 85° C.

7. The process according to claim 1, wherein the spray granulating of said slurry in (c) is performed by spraying said slurry on a fluidized bed of alkali metal salt of aminopolycarboxylic acid (A) particles.

8. The process according to claim 7, wherein the particles in the fluidized bed have an average diameter (D50) in a range of from 100 to 800 µm.

9. The process according to claim 1, wherein the aqueous slurry subjected to spray-granulation in (c) further comprises at least one additive selected from silica, silicates, and organic (co)polymers.

10. The process according to claim 1, wherein alkali metal salt of aminopolycarboxylic acid (A) is selected from compounds according to general formula (I)

$$[CH_3-CH(COO)-N(CH_2-COO)_2]M_{3-x}H_x \qquad (I)$$

wherein

M is selected from alkali metal cations, same or different, and x is in a range of from zero to 1.0.

11. The process according to claim 1, wherein the slurry is spray granulated with a gas inlet temperature of at least 150° C. for an average residence time ranging from 30 minutes to 2 hours, .

12. The process according to claim 1, wherein the granules have an average particle diameter (D50) in the range of from 0.4 mm to 1.25 mm.

\* \* \* \* \*